(12) United States Patent
Gusyatiner et al.

(10) Patent No.: US 7,052,884 B2
(45) Date of Patent: *May 30, 2006

(54) **L-ARGININE PRODUCING *ESCHERICHIA COLI* AND METHOD OF PRODUCING L-ARGININE**

(75) Inventors: Mikhail Markovich Gusyatiner, Moscow (RU); Tatyana Viktorovna Leonova, Moscow (RU); Leonid Romanovich Ptitsyn, Moscow (RU); Tatyana Abramovna Yampolskaya, Moscow (RU)

(73) Assignee: Ajinomoto Co., Inc., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 10/924,798

(22) Filed: Aug. 25, 2004

(65) Prior Publication Data

US 2005/0026259 A1 Feb. 3, 2005

Related U.S. Application Data

(62) Division of application No. 09/886,254, filed on Jun. 22, 2001, now Pat. No. 6,841,365.

(30) Foreign Application Priority Data

Jul. 6, 2000 (RU) ............................. 2000117677

(51) Int. Cl.
*C12N 1/20* (2006.01)
*C12P 13/10* (2006.01)

(52) U.S. Cl. .............. 435/114; 435/252.33; 435/252.8; 435/849

(58) Field of Classification Search ........... 435/252.33, 435/252.8, 114, 849
See application file for complete search history.

(56) References Cited

U.S. PATENT DOCUMENTS

| | | | |
|---|---|---|---|
| 4,430,430 A * | 2/1984 | Momose et al. ............. | 435/114 |
| 4,775,623 A * | 10/1988 | Katsumata et al. .......... | 435/114 |
| 5,017,482 A * | 5/1991 | Katsumata et al. .......... | 435/114 |
| 5,175,107 A | 12/1992 | Debabov et al. | |
| 5,538,873 A | 7/1996 | Debabov et al. | |
| 5,631,157 A | 5/1997 | Debabov et al. | |
| 5,976,843 A | 11/1999 | Debabov et al. | |
| 6,165,756 A | 12/2000 | Debabov et al. | |
| 6,297,031 B1 | 10/2001 | Debabov et al. | |
| 6,653,111 B1 | 11/2003 | Debabov et al. | |
| 6,737,255 B1 | 5/2004 | Livshits et al. | |
| 6,790,647 B1 | 9/2004 | Ptitsyn et al. | |
| 6,841,365 B1 * | 1/2005 | Gusyatiner et al. ......... | 435/114 |
| 2002/0034793 A1 | 3/2002 | Gusyatiner et al. | |
| 2002/0058315 A1 | 5/2002 | Lunts et al. | |
| 2003/0129708 A1 | 7/2003 | Pittsyn et al. | |
| 2003/0148474 A1 | 8/2003 | Gusyatiner et al. | |
| 2004/0191876 A1 | 9/2004 | Lunts et al. | |

FOREIGN PATENT DOCUMENTS

| | | |
|---|---|---|
| JP | 56-106598 | 8/1981 |
| JP | 57-5693 | 1/1982 |

OTHER PUBLICATIONS

A. Pierard, et al., Molec. Gen. Genet., vol. 118, pp. 235-245, "Mutations Affecting Uridine Monophosphate Pyrophosphorylase or the Argr Gene in *Escherichia coli*", 1972.

N. Glansdorff, "Biosynthesis of Arginine and Polyamines", pp. 408-433, 1996.

K. McQuillen, et al., Chemical Abstract of J. Biol. Chem., vol. 207, pp. 81-95, AN 1954-32938, "The Utilization of Acetate for Synthesis in *Escherichia coli*", 1954.

M. Adam, et al., Chemical Abstract of FEMS (Federation of European Microbiological Societies) Microbiology Letters, vol. 110, No. 3, pp. 265-268, "Insertional Mutagenesis to Isolate Acetate-Requiring Mutants in Chlamydomonas Reinhardtii", 1993.

M. Baetens, et al., Microbiology, vol. 144, No. 2, pp. 479-492, "Genes and Enzymes of the Acetyl Cycle of Arginine Biosynthesis in the Extreme Thermophilic Bacterium Thermus Thermophilus HB27", 1998.

Cutinelli et al, "Acetic Acid Metabolism in *Escherichia coli*", Acta Chemica Scandinavica 5, (1951), pp. 353-371.

* cited by examiner

*Primary Examiner*—Herbert J. Lilling
(74) *Attorney, Agent, or Firm*—Oblon, Spivak, McClelland, Maier & Neustadt, P.C.

(57) ABSTRACT

Arginine can be efficiently produced by cultivating *Escherichia coli* which has an ability to produce arginine and an ability to utilize acetate in a culture medium to produce and accumulate arginine in the medium, and collecting arginine from the medium.

6 Claims, 1 Drawing Sheet

L-ARGININE PRODUCING *ESCHERICHIA COLI* AND METHOD OF PRODUCING L-ARGININE

CROSS-REFERENCE TO RELATED APPLICATIONS

The present application is a Divisional Application of U.S. application Ser. No. 09/886,254 now U.S. Pat. No. 6,841,365, filed on Jun. 22, 2001, which claims priority to RU 2000117677, filed on Jul. 6, 2000.

BACKGROUND OF THE INVENTION

1. Field of the Invention

The present invention relates to L-arginine producing *Escherichia coli* and a method of producing L-arginine by fermentation using *Escherichia coli*. L-arginine is an industrially useful amino acid as ingredients of liver function promoting agents, amino acid transfusions, comprehensive amino acid preparations and the like.

2. Description of the Related Art

It is known that some mutants of *Escherichia coli* resistant to analogs of arginine and pyrimidines produce arginine (Pierard A. and Glansdorf N., *Mol. Gen. Genet.*, 118, 235, 1972. and Glansdorf N., Biosynthesis of arginine and polyamines. In "*E. coli* and *Salm. thyphimurium*, 1996). Additionally, the methods for producing arginine using mutants of *E. coli* resistant to some other drugs or recombinant strain of *E. coli* into which a gene encoding an enzyme of arginine biosynthetic pathway is introduced are known.

In arginine biosynthetic pathway of *E. coli* K12 one mole of acetyl-CoA is consumed and one mole of acetic acid is released to produce one molecule of arginine (FIG. 1). As a result of the acetate by-production, a significant part of carbon source is wasted, besides, the accumulation of acetate worsens the growth of culture of arginine producers.

It is also known that *E. coli* can not effectively utilize acetate as carbon source.

SUMMARY OF THE INVENTION

Figure 1:
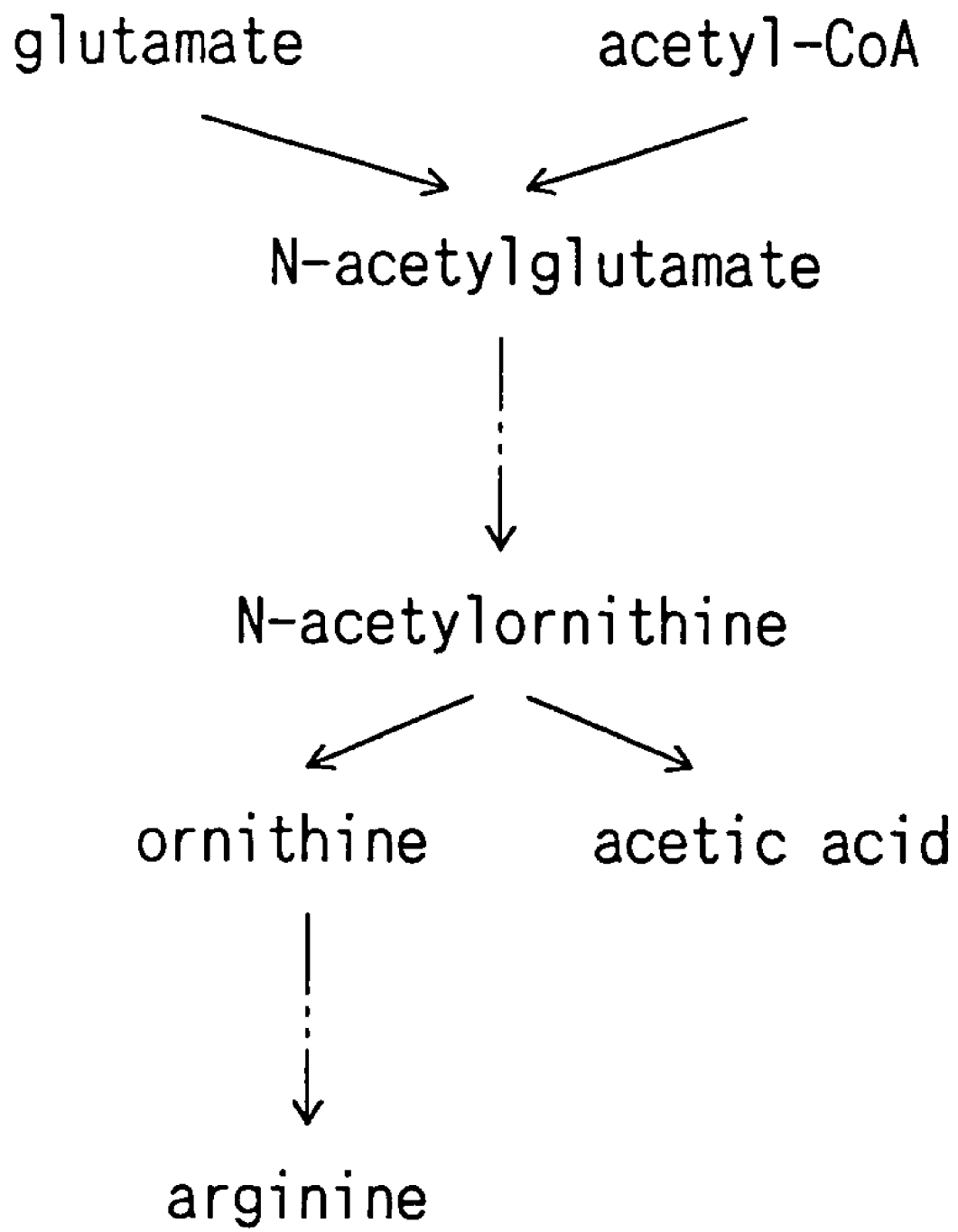
FIG. 1 shows a schematic representation of the arginine biosynthetic pathway of *E. coli* K12.

From the above point of view, the present inventors conceived that the arginine production would be higher, if strains producing arginine had ability to re-utilize acetic acid. Accordingly, an object of the present invention is to provide arginine producing strain of *E. coli* which utilize acetic acid and a method for producing arginine using the strain.

Then the inventors constructed mutants of *E. coli* arginine producer which can utilize acetic acid and have succeeded in improving the arginine productivity of the *E. coli* arginine producer. Thus the present invention has been accomplished.

That is, the present invention provides *Escherichia coli* which has an ability to produce arginine and an ability to utilize acetate.

The present invention further provides a method of producing arginine comprising the steps of cultivating *E. coli* strain which has an ability to utilize acetate and an ability to produce arginine, in a culture medium to produce and accumulate arginine in the medium, and collecting arginine from the medium.

In the present invention, an amino acid is of L-configuration.

The present invention will be explained in detail below.

*E. coli* of the present invention has an ability to utilize acetate and an ability to produce arginine. *E. coli* strain having the ability to utilize acetate and the ability to produce arginine may be obtained by imparting the ability to utilize acetate to *E. coli* strain having the ability to produce arginine, or by imparting the ability to produce arginine to *E. coli* strain having the ability to utilize acetate.

For the present invention, the term "ability to produce arginine" refers to an ability of *E. coli* strain used for the present invention to produce and accumulate arginine in a medium when the *E. coli* strain is cultivated in the medium. The term "ability to utilize acetate" refers to an ability to metabolize acetic acid or acetate more efficiently than the parental strain, for example, an ability of *E. coli* strain used for the present invention to grow faster than the parental strain when the *E. coli* strain is cultivated in a medium containing acetic acid or acetate as a sole carbon source. More concretely, it can be said that *E. coli* strain has ability to utilize acetate if the strain grows faster than the parental strain when the strains are cultivated in a medium containing acetic acid or acetate as a sole carbon source, for example, the liquid minimal medium A (described below) containing 5 g/L of ammonium acetate under an appropriate condition. Most concretely, it can be said that *E. coli* strain has ability to utilize acetate if the strain forms a colony within 2 days at 37° C. when the strain is cultivated on an agar medium containing acetic acid or acetate as a sole carbon source, for example, the minimal medium A (described below) containing 5 g/L of ammonium acetate and agar under an appropriate condition. The term "an appropriate condition" refers to temperature, pH, air supply or optional presence of essential nutrients or the like for the *E. coli* strain which is to be cultivated.

As an example of a method for obtaining *E. coli* of the present invention, a method of inducing a mutant having an ability to utilize acetate from *E. coli* strain having an ability to produce arginine will be explained below.

*E. coli* having an ability to produce arginine is not specifically limited, provided that it can be imparted an ability to utilize acetate. Such *E. coli* strains include arginine-producing strains bred from *E. coli* K-12, B, C, or those derivatives.

As examples of the *E. coli* arginine producer, the following may be mentioned: a mutant having resistance to α-methylmethionine, p-fluorophenylalanine, D-arginine, arginine hydroxamate, s-(2-aminoethyl)-cysteine, α-methylserine, β-2-thienylalanine or sulfaguanidine (Japanese Laid-Open Publication No. 56-106598), arginine-producing strain into which argA gene encoding N-acetylglutamate synthetase is introduced (Japanese Laid-Open Publication No. 57-5693) and the like. *E. coli* strain 237 which is described in after-mentioned Examples is also preferable arginine-producing strain. The strain 237 has been deposited in Russian National Collection of Industrial Microorganisms (VKPM) under the accession number VKPM B-7925 since Apr. 10, 2000, and transferred to the original deposit to international deposit based on Budapest Treaty, on May 18, 2001.

A mutant strain having an ability to utilize acetate may be obtained from an arginine-producing strain as described above by, for example, mutagenizing the arginine-producing strain and selecting strains which can grow in a minimal medium containing acetic acid or acetate as a sole carbon source. Mutagenesis can be performed by, for example, UV irradiation or with an agent usually used for artificial mutagenesis such as 1-methyl-3-nitro-1-nitrosoguanidine (NTG) and nitrous acid. Mutagenesis and selection of a mutant strain having an ability to utilize acetate may be repeated two or more times.

Arginine can be efficiently produced by cultivating the *E. coli* strain described above, which has the activity to utilize acetate and to produce arginine, in a culture medium to produce and accumulate arginine in the medium, and collecting arginine from the medium.

Acetylation of glutamate to N-acetylglutamate and deacetylation of N-acetylornithine to ornithine in arginine biosynthesis of coryneform bacteria are catalyzed by the same enzyme, ornithine acetyltransferase. On the other hand, acetylation and deacetylation in arginine biosynthesis of *E. coli* are catalyzed by different enzymes, N-acetylglutamate synthase and N-acetylornithinase, respectively. Therefore, if by-produced acetic acid would be utilized, its effect on arginine production has been unknown.

In the method for producing arginine of present invention, the cultivation of *E. coli*, the collection and purification of arginine from the liquid medium may be performed in a manner similar to the conventional fermentation method wherein arginine is produced using *E. coli*.

As the carbon source, it is possible to use sugars such as glucose, lactose, galactose, fructose, or starch hydrolysate; alcohols such as glycerol or sorbitol; or organic acids such as acetic acid, fumaric acid, citric acid or succinic acid.

As the nitrogen source, it is possible to use inorganic ammonium salts such as ammonium sulfate, ammonium chloride or ammonium phosphate; organic nitrogen such as soybean hydrolysate; ammonia gas; or aqueous ammonia.

It is desirable to allow required substances such as, vitamin $B_1$ and L-isoleucine or yeast extract to be contained in appropriate amounts as organic trace nutrients. Other than the above, potassium phosphate, magnesium sulfate, iron ion, manganese ion and the like are added in small amounts, if necessary.

Cultivation is preferably carried out under an aerobic condition for 16–72 hours. The cultivation temperature is controlled at 25° C. to 45° C., and pH is controlled at 5–8 during cultivation. Inorganic or organic, acidic or alkaline substances as well as ammonia gas or the like can be used for pH adjustment.

Collection of arginine from fermented liquor is usually carried out by combining an ion exchange resin method and other known methods.

BEST MODE FOR CARRYING OUT THE INVENTION

Hereafter, the present invention will be explained more specifically with reference to the following examples.

EXAMPLE 1

Induction of Acetate Utilizing Mutants

From the arginine-productive mutant *E. coli* strain 237, mutants which grew well on the M9 agar medium containing ammonia acetate (5 mg/ml) as a sole carbon and nitrogen source were induced. The strain 237 is a mutant resistant to a pyrimidine analog, 6-azauracil, which was induced from *E. coli* K12 ilvA::Tn5 by using 1-methyl-3-nitro-1-nitrosoguanidin (NTG). The strain 237 grows poorly on M9 agar containing ammonia acetate as a sole carbon and nitrogen source. The strain 237 has been deposited in Russian National Collection of Industrial Microorganisms (VKPM) under accession number VKPM B-7925 since Apr. 10, 2000, and transferred to the original deposit to international deposit based on Budapest Treaty, on May 18, 2001.

Cells of the strain 237 were grown overnight in L-broth with shaking (test-tube, 37° C.) and harvested by centrifugation. Then, the cells were resuspended in saline solution (0.8%) containing 0.1 mg/ml of NTG. After 30 min of exposure to NTG at 37° C. the cells were spun down, washed twice with saline and plated on the minimal agar medium A, containing 5 g ammonia acetate, 6 g $Na_2HPO_4$, 3 g $KH_2PO_4$, 0.5 g NaCl, 0.1 mg thiamin, 0.1 g L-isoleucine, 15 g agar, per 1 liter of water (pH 7.0).

The plates were incubated for 5 days at 37° C. Colonies appeared within 2 days on the plates were picked up and purified by streaking on the same agar plates. The parental strain 237 formed colonies only after 5 day's cultivation. Frequency of acetate utilizing mutant was $6 \times 10^{-5}$. Seventy purified strains were tested for their productivity of arginine. About ¼ of the mutants derived was more productive than parent strain 237. The best arginine producer among them was strain 382. The strain 382 has been deposited in Russian National Collection of Industrial Microorganisms (VKPM) under the accession number VKPM B-7926 since Apr. 10, 2000, and transferred to the original deposit to international deposit based on Budapest Treaty, on May 18, 2001.

EXAMPLE 2

Growth of the Novel Mutants on Acetate

Two ml portions of the liquid minimal medium A (agar was not added), containing either ammonia acetate (5 g/L) or glucose (5 g/L) as sole carbon sources, were placed into test tubes, inoculated with one loop of the novel strain 382, another example of arginine producing mutant, strain 383 and their parent strain 237, and incubated for 16 hours at 32° C. with shaking. The growth was determined by measuring optical density of the culture at 540 nm. The Optical density of the media at the start of the culture was about 0.05. The results are shown in Table 1.

TABLE 1

| Strain | Growth (OD540) in liquid minimal medium For 16 hours with: | |
|---|---|---|
| | Glucose (0.5%) | Ammonia acetate(0.5%) |
| 237 (parent) | 1.8 | 0.4 |
| 382 | 1.5 | 1.0 |
| 383 | 1.6 | 0.7 |

EXAMPLE 3

Production of Arginine by the Novel L-arginine Producing Mutants in Test-tube Fermentation The novel strain 382, 383 and their parent strain 237 were cultivated in the fermentation medium. The fermentation medium contained 60 g glucose, 25 g ammonia sulfate, 2 g $KH_2PO_4$, 1 g $MgSO_4.7H_2O$, 0.1 mg thiamine, 5 g yeast extract (Difco), 25 g calcium carbonate, per 1 liter of tap water (pH 7.2). Glucose and chalk were sterilized separately. Two ml portions of the medium were placed into test-tubes, inoculated with one loop of the tested microorganisms, and the cultivation was carried out at 32° C. for 3 days with shaking. The accumulated amount of arginine in the culture medium shown in Table 2.

TABLE 2

| Strain | Arginine (g/L) |
|---|---|
| 237 (parent) | 5.1 |
| 382 (acetate utilizing mutant) | 12.0 |
| 383 (acetate utilizing mutant) | 7.7 |

EXAMPLE 4

Production of Arginine by the Novel L-arginine Producing Mutant in Jar Fermenter The novel strain 382 and its parent strain 237 were cultivated with shaking at 32° C. for 8 hours in L-broth. Then, 60 ml of the resulted seed culture were inoculated into 1 liter jar fermenter containing 0.5 L of the a fermentation media, followed by culturing with stirring at 700 rpm at 32° C. and aeration rate 0.5 liter/min. The fermentation medium contained 100 g glucose, 9 g ammonia sulfate, 1 g $KH_2PO_4$, 0.4 g $MgSO_4.7H_2O$ 0.02 g $FeSO_4 .7H_2O$, 0.02 g $MnSO_4.7H_2O$, 0.2 g total nitrogen of Soybean hydrolysate, 0.3 g L-isoleucine, 0.4 mg thiamine in 1 liter of tap water (pH 7.0). During the cultivation, ammonia solution (4.7 M) was added to adjust pH to 7.0 and to supply a nitrogen source. The cultivation was carried out for 42 hours. The accumulated amount of arginine in the culture medium and the yield from glucose are shown in Table 3.

TABLE 3

| Strain | Arginine (g/L) | Yield from glucose (%) |
|---|---|---|
| 237 (parent) | 4.5 | 5.2 |
| 382 (acetate utilizing mutant) | 19.3 | 23.9 |

The acetate-utilizing mutant showed higher productivity of arginine than parental strain.

What is claimed is:

1. A mutant strain of *Escherichia coli* which has an ability to produce and accumulate arginine, and which is modified to grow faster than the parental strain of the mutant strain when the *Escherichia coli* strain is cultivated in a medium containing acetic acid or acetate as a sole carbon source.

2. The mutant stain of *Escherichia coli* according to claim 1, wherein the parental strain is *Escherichia coli* K-12.

3. A method of producing arginine, comprising cultivating the mutant strain of *Escherichia coli* of claim 1 in a medium to produce and accumulate arginine in the medium; and collecting the arginine from the medium.

4. A method of producing arginine, comprising cultivating the *Escherichia coli* of claim 2 in a medium to produce and accumulate arginine in the medium; and collecting the arginine from the medium.

5. The mutant strain of *Escherichia coli* according to claim 1, which forms a colony within 2 days at 37° C. when the strain is cultivated on an agar medium containing 5 g/L of ammonium acetate under an appropriate condition.

6. A method of producing arginine, comprising cultivating the mutant strain of *Escherichia coli* of claim 5 in a medium to produce and accumulate arginine in the medium; and collecting the arginine from the medium.

* * * * *